United States Patent
Dix et al.

(10) Patent No.: US 10,706,962 B1
(45) Date of Patent: Jul. 7, 2020

(54) APPARATUS AND SYSTEM FOR VERIFYING ACCOMPLISHMENT OF AN ACTIVITY WHICH UTILITIZES PENALTIES OR ACCOUNTABILITY FEES TO ENCOURAGE PERFORMANCE OF AN ACTIVITY

(71) Applicants: Charles Dix, Dallas, TX (US); William Tilk, Los Angeles, CA (US)

(72) Inventors: Charles Dix, Dallas, TX (US); William Tilk, Los Angeles, CA (US)

( * ) Notice: Subject to any disclaimer, the term of this patent is extended or adjusted under 35 U.S.C. 154(b) by 142 days.

(21) Appl. No.: 15/885,892

(22) Filed: Feb. 1, 2018

Related U.S. Application Data (63) Continuation-in-part of application No. 14/734,946, filed on Jun. 9, 2015, now abandoned.

(60) Provisional application No. 62/010,161, filed on Jun. 10, 2014.

(51) Int. Cl.
| | |
|---|---|
| *G16H 20/30* | (2018.01) |
| *G16H 40/67* | (2018.01) |
| *G06Q 10/10* | (2012.01) |
| *A63B 24/00* | (2006.01) |
| *G09B 19/00* | (2006.01) |

(52) U.S. Cl.
CPC .......... *G16H 20/30* (2018.01); *A63B 24/0059* (2013.01); *G06Q 10/109* (2013.01); *G09B 19/003* (2013.01); *G16H 40/67* (2018.01)

(58) Field of Classification Search
CPC .. G09B 19/003; G09B 19/0038; G06Q 50/22; G06Q 50/24
See application file for complete search history.

(56) References Cited

U.S. PATENT DOCUMENTS

| | | | | |
|---|---|---|---|---|
| 2010/0197463 | A1* | 8/2010 | Haughay, Jr. ...... | A63B 24/0062 482/8 |
| 2010/0223075 | A1* | 9/2010 | Sparks ................... | G06Q 30/02 705/3 |
| 2010/0227302 | A1* | 9/2010 | McGilvery ........ | G09B 19/0038 434/236 |
| 2012/0116550 | A1* | 5/2012 | Hoffman ............ | A63B 24/0084 700/91 |
| 2013/0117043 | A1 | 5/2013 | Condon | |

(Continued)

*Primary Examiner* — Peter R Egloff
(74) *Attorney, Agent, or Firm* — Michael Diaz (57) ABSTRACT

A system for monitoring the accomplishment of an activity of a user. The system includes an activity monitoring system for monitoring the accomplishment of an assigned physical activity of the user. The activity monitoring system includes data storage and an activities compiler for storing information associated with the assigned physical activity for the user of the system. The system also includes an interactive communication and verification (ICV) apparatus which accumulates information related to the accomplishment of the assigned activity. The ICV apparatus sends the accumulated information to the activity monitoring system. The activity monitoring system stores a predefined activity parameter and penalty/accountability fee assessment. The activities compiler compiles the accumulated information received from the user and determines if the assigned physical activity is performed based on the predefined activity parameter. If the physical activity is not correctly performed, the compiler assesses the penalty/accountability fee assessment.

15 Claims, 5 Drawing Sheets

(56) References Cited

U.S. PATENT DOCUMENTS

2014/0266630 A1\* 9/2014 Beckman .......... G06K 7/10366
340/10.5
2015/0201888 A1 7/2015 Vachon et al.

\* cited by examiner

APPARATUS AND SYSTEM FOR VERIFYING ACCOMPLISHMENT OF AN ACTIVITY WHICH UTILITIZES PENALTIES OR ACCOUNTABILITY FEES TO ENCOURAGE PERFORMANCE OF AN ACTIVITY

RELATED APPLICATIONS

This application is a continuation-in-part application of co-pending U.S. patent application Ser. No. 14/734,946 entitled "System and Method of Using a Penalty/Accountability Fee to Encourage an Activity" filed on Jun. 9, 2015 which claims the benefit of U.S. Provisional patent application Ser. No. 62/010,161 filed Jun. 10, 2014 by Charles Dix and William Tilly which is hereby incorporated by reference.

BACKGROUND OF THE INVENTION

Field of the Invention

This invention relates to interactive communication devices. Specifically, and not by way of limitation, the present invention relates to an apparatus and system for confirming the accomplishment of an activity

Description of the Related Art

The consistent accomplishment of various types of physical exercises directly results in the improved health of an individual. Thus, the overall physical wellbeing of a person is based in large measure on executing a routine exercise regimen. Many people wish to maintain an exercise program but fail to maintain the program after even just a few weeks. In the world of a fitness program, many people also employ a trainer to teach, motivate and direct an individual's workout program. However, the trainer is not always present, and it is incumbent upon the individual to perform certain workout activities outside of their training sessions with a trainer. The individual must perform these outside activities without the supervision or motivation of the trainer. Quite frequently, because there is no monitoring or accountability held by these people, the assigned outside activities do not always get accomplished. Without performing these activities (e.g., additional workout sessions), the individual's entire workout program is typically doomed to failure. An apparatus and system are needed which can determine if an individual actually performs a specific exercise assignment for a predetermined time and location as well as a predetermine duration.

Although there are no known prior art teachings of a solution to the aforementioned deficiency and shortcoming such as that disclosed herein, prior art references that discuss subject matter that bears some relation to matters discussed herein are U.S. Publication No. 2015/0201888 to Vachon et al. (Vachon) and U.S. Publication No. 2013/0117043 to Condon (Condon). Vachon discloses a system for incentivizing wellness of employees by measuring a person's wellness score. Vachon is associated with measuring a wellness score, such as using a biometric test. Vachon does not determined if a physical activity was actually accomplished, but rather uses a test to determine if the person's overall health has improved. If a health assessment test improves, inventive points which may equate to some sort of reward are awarded to the individual. Vachon also does not assess a penalty for failure to perform an assigned physical activity. Vachon merely awards the improvement of a wellness score on a health assessment test. Likewise, Condon discloses a wellness incentivizing program which provides a reward to individuals for accomplishing some exercises. But Condon fails to disclose having an apparatus that independently determines if the exercise was actually performed. Condon relies on the honesty of the user to correctly inform the system of the accomplishment of an, exercise. Furthermore, Condon does not assess penalties for failure to perform the physical activity.

An apparatus and system are needed which can independently verify if a physical activity is actually performed at a predetermined time, location and duration while assessing a penalty or accountability fee for failure to accomplish such an activity in the prescribed manner. It is the object of the present invention to provide such an apparatus and system.

SUMMARY OF THE INVENTION

In one aspect, the present invention is a system for monitoring the accomplishment of an activity of a user. The system includes a network and a server communicating with the network. The system also includes an activity monitoring system for monitoring the accomplishment of an assigned physical activity of the user. The activity monitoring system includes data storage and an activities compiler for storing information associated with the assigned physical activity for the user of the system. Furthermore, the system includes an interactive communication and verification (ICV) apparatus connected to the network which accumulates information related to the accomplishment of the assigned physical activity, The ICV apparatus sends the accumulated information to the activity monitoring system. The activity monitoring system receives and stores a predefined activity parameter and penalty/accountability fee assessment for failure to complete the scheduled activity within the predefined activity parameter within the data storage. The activities compiler compiles the accumulated information received from the user and determines if the assigned physical activity is performed based on the predefined activity parameter. If the physical activity is not correctly performed, the compiler assesses the penalty/accountability fee assessment. In one embodiment, the system may also include a supervisor communication device communicating with the activity monitoring system through the network for monitoring the activity of the user, In another aspect of the present invention, the present invention is a computer implemented method of encouraging the accomplishment of a physical activity assigned to a user. The method begins by an ICV apparatus accumulating information on the accomplishment of a physical activity assigned to the user. The ICV apparatus gathers information relevant for verifying the accomplishment of the assigned physical activity. The ICV then provides the accumulated information and a predefined parameter on the assigned physical activity of the user to an activity monitoring system. The activity monitoring determines from the accumulated information if the assigned physical activity is accomplished. A penalty/accountability fee for failure to complete an activity within the predetermined activity parameter to the activity monitoring system is defined and provided to the activity monitoring system. The activity monitoring system determines if the assigned physical activity is accomplished and, upon determining that the activity is not accomplished in the predefined parameter, automatically assesses the defined penalty/accountability fee to the user by the activity monitoring system.

DESCRIPTION OF THE INVENTION

Figure 1:
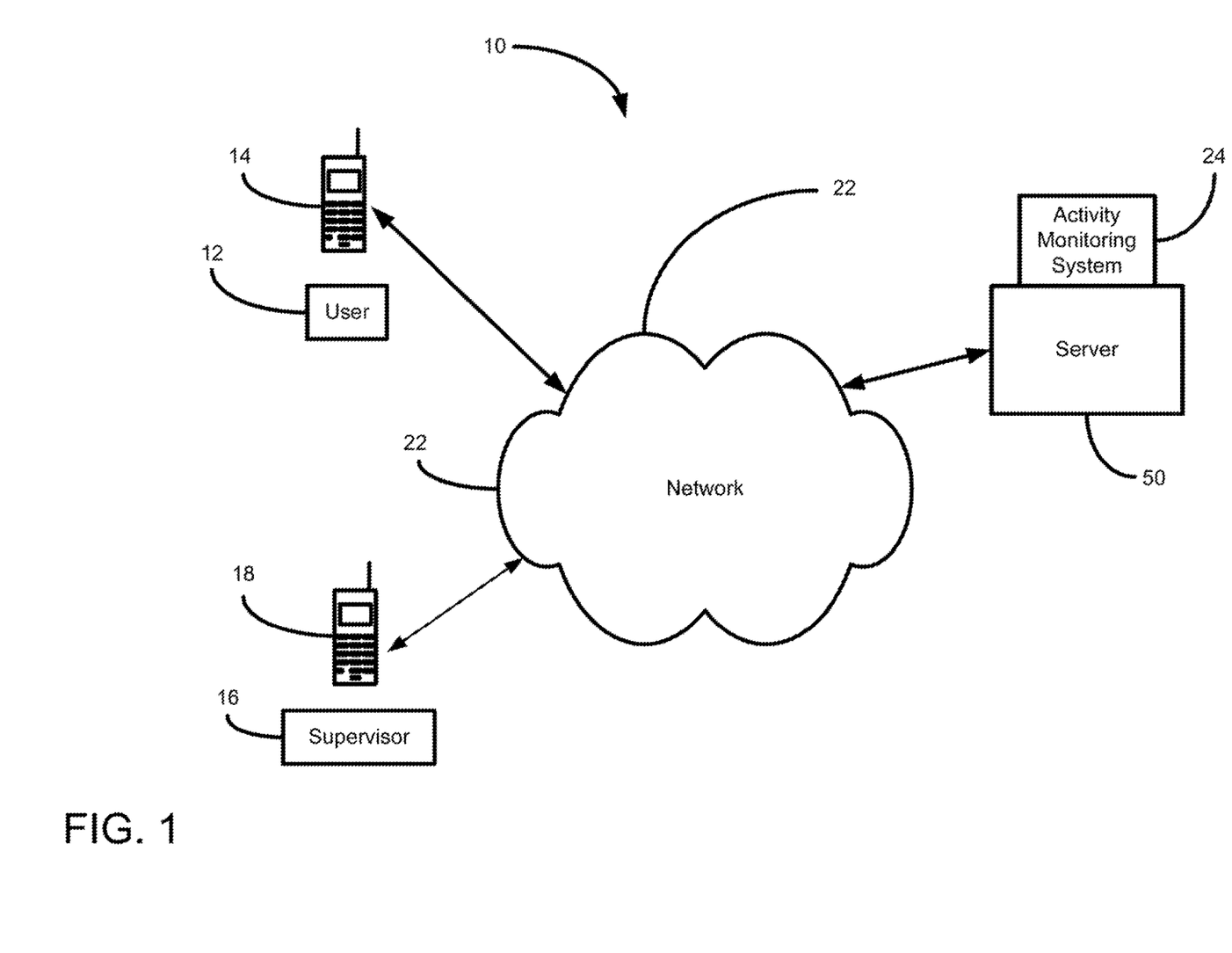
FIG. 1 is a simplified block diagram of key components utilized in an exercise verification and accountability system according to the teachings of the present invention.

The present invention is an apparatus and system for confirming the accomplishment of an activity utilizing penalties and accountability fees to motivate a user to accomplish an activity. FIG. 1 is a simplified block diagram of key components utilized in an exercise verification and accountability system 10 according to the teachings of the present invention. The system 10 includes a user 12 having an interactive communication and verification (ICV) apparatus 14, a supervisor 16 having a communication device 18, and a server 20 having an activity monitoring system 22 operating in a communications network 22, such as the Internet. The user 12 communicates with the activity monitoring system 24 and optionally the supervisor 16 through the ICV apparatus 14. Additionally, the supervisor may communicate with the activity monitoring system 24 and the user 12 through the communication device 18.

Preferably, the ICV apparatus 14 used by the user 12 and the communication device 18 used by the supervisor 16 may be any suitable device operable to act as a client on a network. Illustrative communications terminals include, but are not limited to, mobile phones, personal computers, desktop computers, laptops, servers, including, but not limited to Voice over Internet Protocol (VoIP) telephones, smart telephones, wireless devices, such as cellular telephones, personal digital assistants, tablets, etc. Both the communication device 18 and the ICV apparatus 14 may be configured to transmit and receive information through the network 22.

Figure 2:
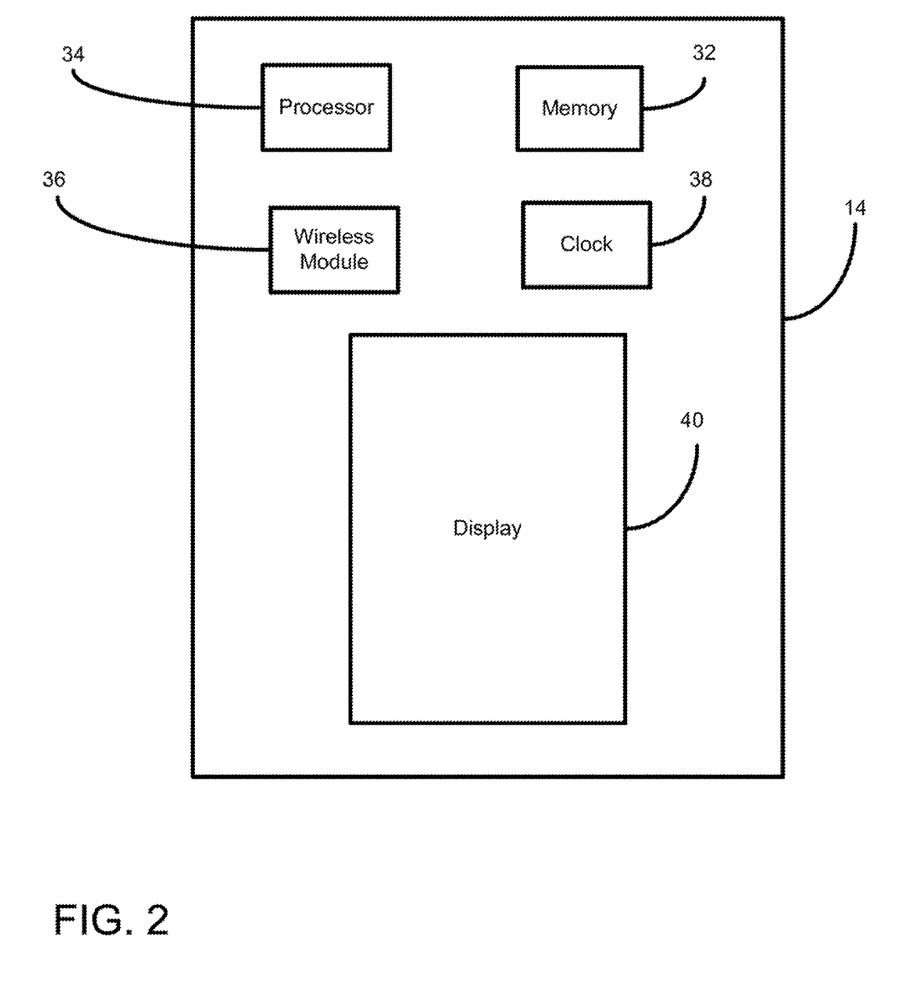
FIG. 2 is a simplified block diagram of some of the key components of the ICV apparatus in one embodiment of the present invention.

FIG. 2 is a simplified block diagram of some of the key components of the ICV apparatus 14 in one embodiment of the present invention. The ICV apparatus may include a location services module 30 (such as a Global Positioning System (GPS) unit) to provide location information of the user's ICV apparatus to the activity monitoring system 24 and/or supervisor 16. Additionally, the ICV apparatus may include a memory 32 for storing a set of instructions and a processor 34 for executing the instructions. The processer may access information from, and store information in a nonremovable memory, a removable memory, or a combination thereof, also collectively referred to herein as computer readable media. Illustrative nonremovable memory may consist of RAM, ROM, a hard disk, or other well-known memory storage technologies. Illustrative removable memory may consist of one or more Subscriber Identity Module (SIM) cards, or other well-known memory storage technologies, such as "smart cards," magnetic disks, floppy disks, optical disks, magneto-optical disks, magnetic tapes, or any suitable non-volatile memory. As will be discussed below, the set of instructions executed by the processor gather and provide information for confirming the accomplished of an assigned exercise by the user to the activity monitoring system 24. The ICV apparatus also includes a wireless module 36, such as a Bluetooth module for communicating with other electronic devices, an internal clock 38 for providing time and time duration of an assigned exercise, and a display 40. The ICV apparatus 14 may utilize various sources of information to verify that a user has actually performed the physical activity. The location services monitor 30 may be used to confirm the correct predetermined location of the activity. The clock 38 may be used to confirm that the activity is performed at the correct predetermined time and for the predetermined duration. The ICV apparatus 14 may be connected, either wirelesses or through a physical conduit with other hardware monitoring devices, such as a fitness band or watch, which may measure vital statistics, such as a heart rate monitor, an accelerometer (typically present in most mobile phones), a blood pressure monitor, a respirator rate monitor, a blood glucose monitor and a weight scale. Many of these measuring or monitoring devices may be a separate device which are connected wirelessly through the wireless module 36 of the ICV apparatus 14. This information is gathered by the ICV apparatus 14 and sent to the activity monitoring system 24 for confirmation that the predetermined activity is performed at the prescribed location (e.g., the gym), time and duration.

The communications network 22 may include any number of networks capable of providing communications between the user (through the ICV apparatus 14) and the activity monitoring system and/or supervisor 16. For example, the communications network may be one or more or any combination of wireless networks, data or packet networks, publicly switched telephone networks (PSTN), Internet, etc.

Figure 3:
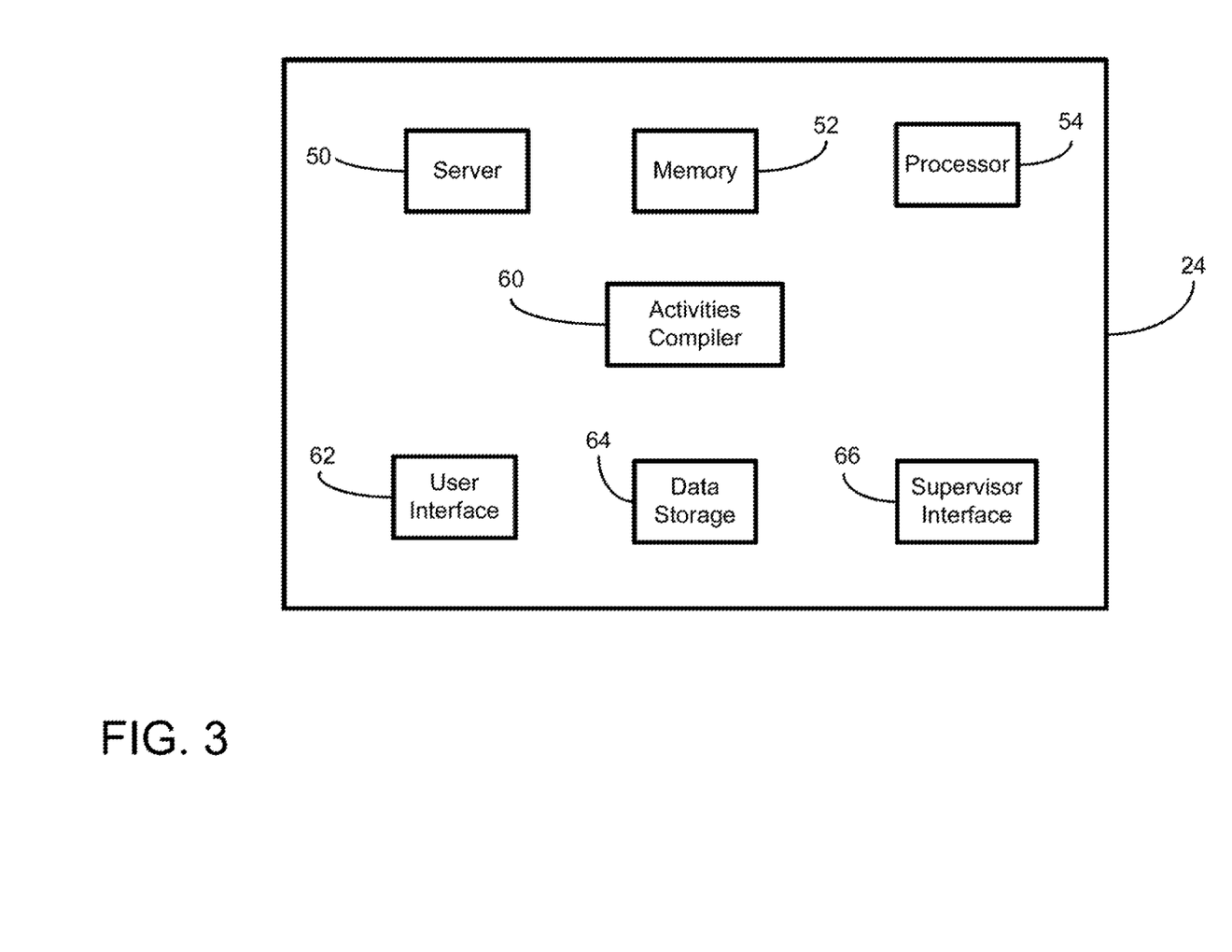
FIG. 3 is a simplified block diagram of key components of the activity monitoring system in one embodiment of the present invention.

The activity monitoring system 24 provides monitoring and compilation of a user's specified activity. FIG. 3 is a simplified block diagram of key components of the activity monitoring system 24 in one embodiment of the present invention. In one embodiment, the activity monitoring system 24 may be coupled with a server 50. The server 50 may be any server, computer or device configured to process information related to the user and the user's specified activities. In one embodiment, the activity monitoring system 24 may include a memory 52 for storing a set of instructions and a processor 54 for executing the instructions. The processer may access information from, and store information in a nonremovable memory, a removable memory, or a combination thereof, also collectively referred to herein as, computer readable media. Illustrative nonremovable memory may consist of RAM, ROM, a hard disk, or other well-known memory storage technologies. Illustrative removable memory may consist of one or more Subscriber Identity Module (SIM) cards, or other well-known memory storage technologies, such as "smart cards," magnetic disks, floppy disks, optical disks, magneto-optical disks, magnetic tapes, or any suitable non-volatile memory. As will be discussed below, the set of instructions executed by the server 50 permit the server to process information related to the user's specified activities.

Still referring to FIG. 3, the activity monitoring system 24 also includes an activities compiler 60, a user interface 62, data storage 64, and a supervisor interface 66. The activities compiler compiles information on the user's activities <by receiving information from the ICV apparatus 14, such as the user's location, time accomplished and duration of the scheduled activity. The user interface 62 enables an interface for a user to communicate with the activities monitoring system 24. In particular, the user interface may include generation and transmittal of a software application or mobile application, commonly referred to as an "app" which is downloaded to the user's ICV apparatus 14. As referred to in the present invention herein, the software application is the application. The application, in one embodiment, may be downloaded to the user's communications device to enable communications with the user interface 62 of the activities monitoring system as well as facilitate transmittal and receipt of information on the user's activities. The data storage 64 may include data related to the user, the user's profile, activities, location of activities, schedule of activities, etc. The supervisor interface 66 may be utilized to provide an interface for the supervisor 16 to communicate with the activities monitoring system 24, thereby allowing the supervisor to monitor the activities of the user as well as communicate information to the user as desired. The activity monitoring system may reside with the server 50 (i.e., separate from the ICV apparatus 14) or co-located with the ICV apparatus 14.

Figure 4:
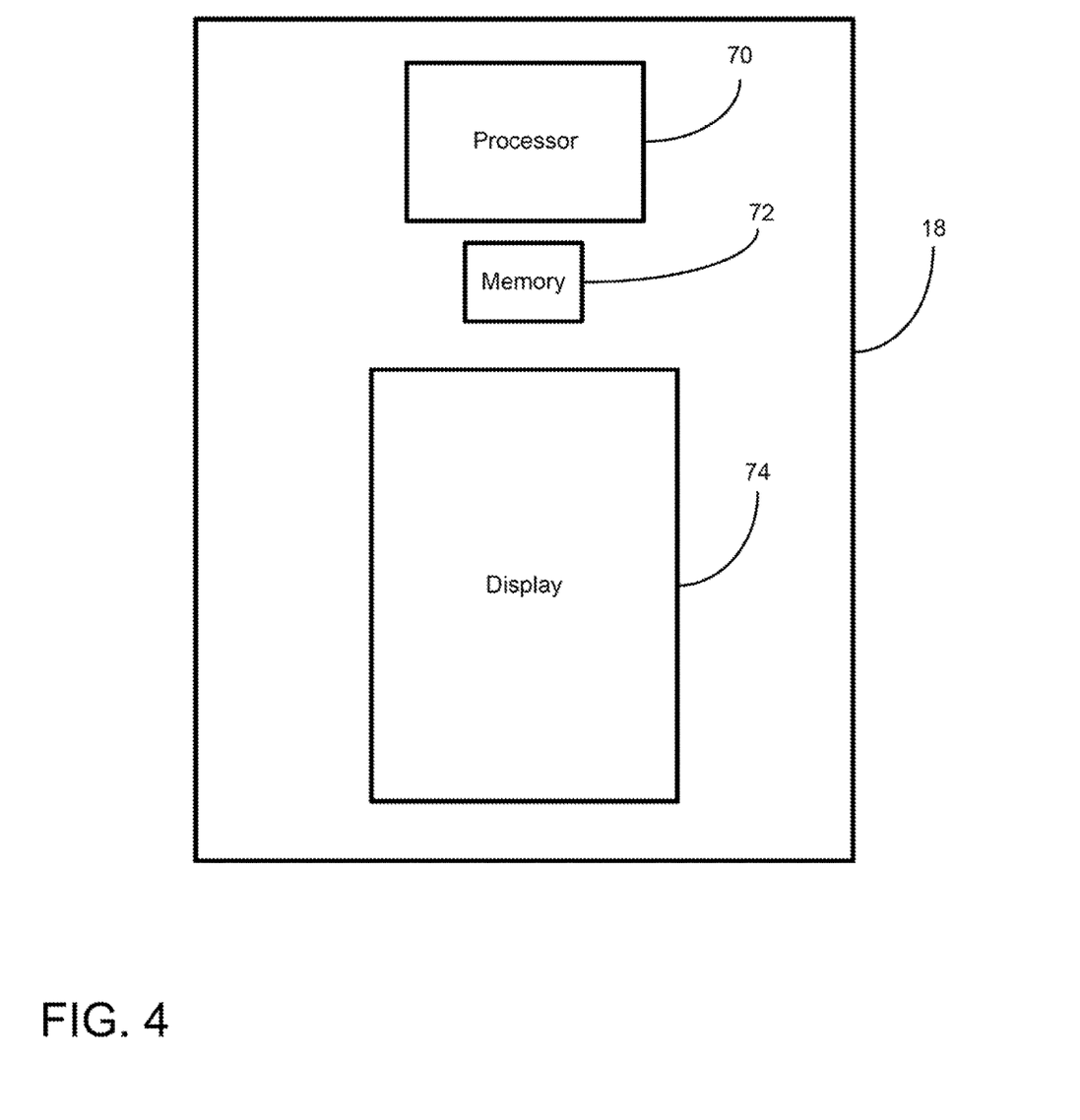
FIG. 4 is a simplified block diagram of the communication device.

As discussed above, in one embodiment, each user may download the application for use in interacting with the activities monitoring system 24. The downloaded application resides in the ICV apparatus 14 and optionally communication device 18. FIG. 4 is a simplified block diagram of the communication device 18, such as a mobile phone used by the supervisor 16. The communications device 18 includes a processor 70, memory 72, and a display 74. The processor and memory may be any mechanism allowing computing services for the communication device 18 and the execution of the downloaded application from the activities monitoring system 22.

The present invention utilizes the ICV apparatus 14 to verify that a predetermined activity is accomplished, The present invention confirms the accomplishment of the activity, and if not, the system utilizes the opposite of a reward, a negative reinforcement to discourage failing to accomplish the task. The system utilizes negative motivation in the form of enacting penalties and/or accountability fees to motivate a user to accomplish an activity. If a user fails to accomplish the predetermined activity in the prescribed manner, the user pays a fee. The user agrees to pay a penalty/accountability fee if a specific activity is not performed and, optionally, at a specific time and place. The present invention monitors the accomplishment of the activity through the ICV apparatus 14 and, if it is determined by the activity monitoring system 24 that the user has not accomplished the specified activities at the specified time, the system automatically assesses the agreed upon penalty/accountability fee. Each time the user fails to accomplish the planned activity, the penalty/accountability fee is assessed. In addition, the present invention enables the supervisor to monitor the activities of the user and the assessed penalty/accountability fees as well as communicate with the user, In one embodiment, all or a portion of the penalty/accountability fees may be given to the supervisor. Thus, the present invention provides an incentive for the user to perform the specified activity by utilizing penalty/accountability fees as an inducement. Additionally, the present invention, enables the supervisor to monitor the activities as well as encouraging the use of the system since the supervisor receives all or a portion of the assessed penalty/accountability fees of the user.

In one embodiment, the present invention may be used in workout training. For example, the user may be a person training with a trainer, in this case, the supervisor, The activity may be a supplemental workout session conducted while not in the presence of the trainer. It is quite common for trainers to assign additional activities to the user to perform, for example 60 minutes of cardio exercise in between supervised training sessions, Since the trainer is not present, the user must use self-discipline to perform the assigned activities. The present invention will ensure that the activities are performed or assess a penalty/accountability fee to the user. As discussed above, the present invention may be embodied in the form of an app providing interactive communication between the user 12 and the system 10.

With reference to FIGS. 1-4, the operation of the system 10 will now be explained. As an example of the present invention, a fitness activity under the supervision of a trainer (supervisor) will be explained, However, it should be understood that the present invention may be used for any physical activity. Additionally, although the present invention is depicted as an app, the present invention may be embodiment in any format and visual display and still remain in the scope of the present invention. In the preferred embodiment of the present invention, an exercise activity is specified with a predefined location, time of event and duration of event. This information is provided to the activity monitoring system which stores the information in the memory 52. This physical activity may be assigned by the supervisor (trainer) and input to the activity monitoring system 24 through the supervisor interface 66 or by the user through the user interface 62. Additionally, an agreed penalty/accountability fee assessment for failure to complete an activity within the predefined activity parameter or parameters is also established and provided to the activity monitoring system 24. When the scheduled time of the activity approaches, the user may check-in for the activity, such as when the user is going to begin an activity, such as a cardio workout at the gym. When the user checks in, the locations services module 30 determines the location of the user through the ICV apparatus 14. The activity is then monitored by the ICV monitor 14 for accomplishment of the task, proper time of accomplishing the task and the proper duration of the task. The ICV apparatus 14 may be connected to other external monitoring hardware, such as a fitness band or watch, which may measure vital statistics, which may include a heart rate monitor, an accelerometer (typically present in most mobile phones), a blood pressure monitor, a respirator rate monitor, a blood glucose monitor and a weight scale. In many of these measuring/monitoring devices, they may be a separate device which is connected wirelessly through the wireless module 36 of the ICV apparatus 14. This information is gathered by the ICV apparatus 14 and used to determine if the activity was actually performed. For example, monitoring an increased heartrate may be indicative of performing a cardiovascular activity. Likewise, monitoring the step count by a fitness band may be used to determine if a walking or running activity has been performed. The information gathered by the ICV apparatus 14 is then sent to the activity monitoring system 24 where the completion of the activity is determined. Specifically, the activity monitoring system 20 may determine if the user is located within a predetermined range of a set location for the activity and optionally within a predetermined time period set for the activity. If the activity monitoring system 24 determines that the user is out of range on either the location or the tine, the activity monitoring system sends an invalid check-in message to the user. The activity monitoring system automatically determines if the activity is performed within the predefined parameter or parameters, and if it is determined that the activity is not performed in the predefined parameter or parameters, assesses a penalty/accountability fee based on the penalty/accountability fee set by the user. In the preferred embodiment of the present invention, the user is automatically charged, typically with a credit card. The penalty/accountability fee provides an incentive to the user to complete the task and avoid paying the penalty/accountability fee. All or a portion of the penalty/accountability fee may be provided to the trainer (supervisor) as an incentive to the trainer to use the system 10. In addition, the app provides information to the trainer on the progress of the user as well as the assessed penalty/accountability fees.

Figure 5:
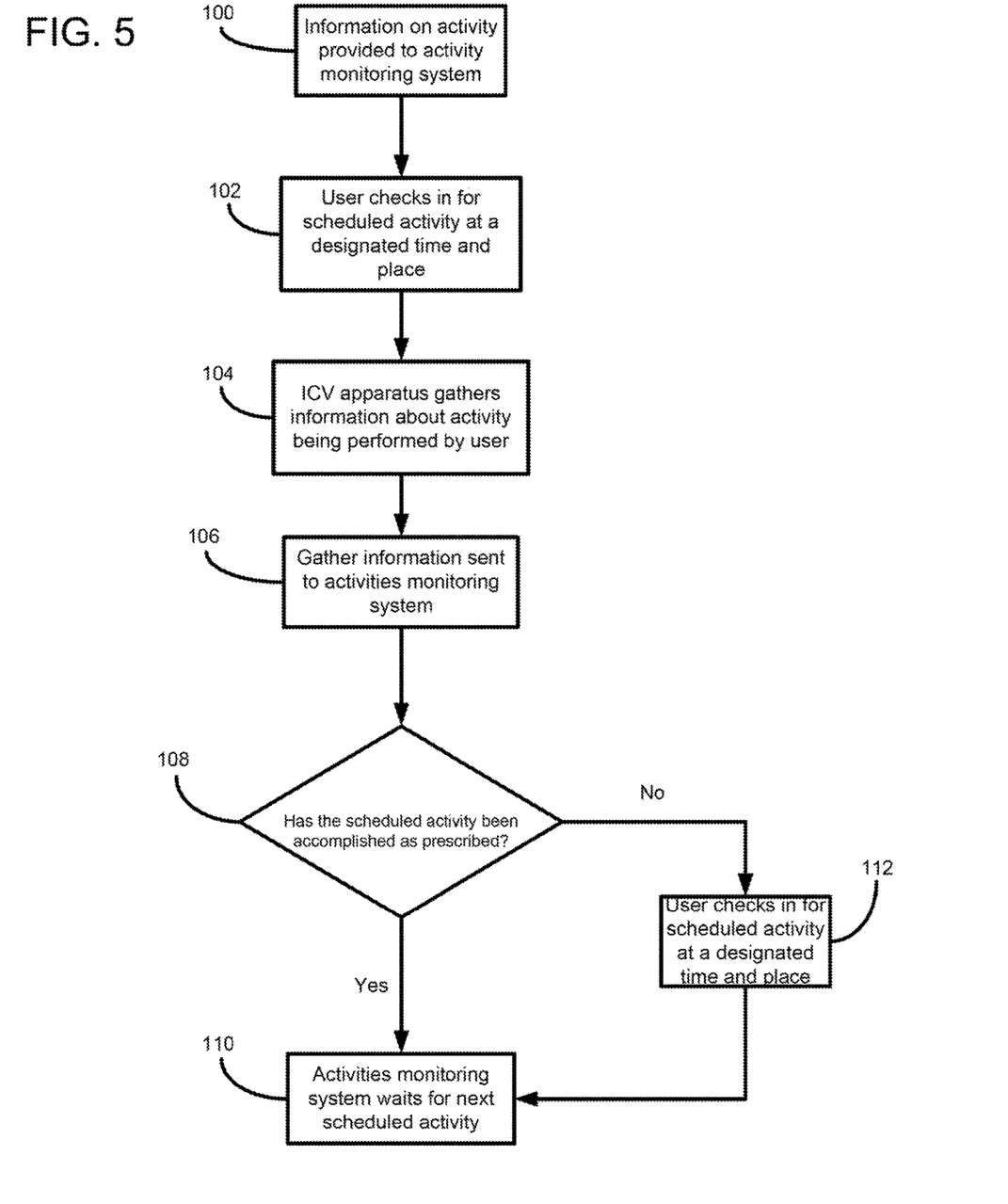
FIG. 5 is a flow chart of the steps of a method of using the ICV apparatus and the system according to the teachings of the present invention.

FIG. 5 is a flow chart of the steps of a method of using the ICV apparatus 14 and the system 10 according to the teachings of the present invention. With reference to FIGS. 1-5, the method will now be explained. The method begins in step 100 where information on a scheduled physical activity is provided to the activity monitoring system 24. The supervisor 16 through the communication device 18 or the user 12 through the ICV apparatus 14 may input the requisite information to allow the activity monitoring system 24 to ascertain whether an activity is accomplished. This information may include the time when the activity should be accomplished, the location of the activity, the type of activity and the duration of the activity. Furthermore, information on the penalty fee or accountability fee which the user must pay if the user fails to accomplish the activity is entered. Next, in step 102, the user checks in with the system 10 through the ICV apparatus 14 when beginning the exercise activity. The method then moves to step 104 where the ICV apparatus 14 gathers the information necessary to verify completion of the activity, such as the location of the user at the predetermined time and for the predetermined duration. As defined for the specified exercise, the ICV apparatus 14 gathers any additional information relevant for determining the accomplishment of the specified exercise. This may include gathering information from external devices such as fitness bands or watches, where vital statistics of the user may be monitored. Next, in step 106, the gathered information is sent to the activities monitoring system 24. In step 108, the activity monitoring system 24 determines if the user has accomplished the scheduled activity (optionally at the designated time and location within a predetermined range) within the predefined parameter or parameters. If the scheduled activity has been accomplished within the predefined parameter or parameters, the method movies to step 110 where the activity monitor system 24 awaits the next activity and check-in from the user. However, in step 108, if it is determined that the user did not accomplish the scheduled activity within the predefined parameter or parameters, the method moves to step 112 where the activity monitoring system 24 assesses a penalty/accountability fee upon the user. The method then moves to step 110 where the activity monitor system 24 awaits the next activity and check-in from the user. In the preferred embodiment of the present invention, the present invention is utilized for performing a physical exercise. However, it should be understood that the present invention may be used for any activity.

The present invention provides many advantages to users wishing to accomplish activities. The present invention encourages the user to accomplish a task by using penalty/accountability fees as a motivational tool in performing the assigned task. By using penalties and accountability fees, the user ends of paying additional fees for failure to perform. This negative motivation provides an effective tool in modifying a user's behavior. The present invention monitors and verifies the accomplishment of a task, and if not accomplished, automatically assesses a penalty/accountability fee on the user.

While the present invention is described herein with reference to illustrative embodiments for particular applications, it should be understood that the invention is not limited thereto. Those having ordinary skill in the art and access to the teachings provided herein will recognize additional modifications, applications, and embodiments within the scope thereof and additional fields in which the present invention would be of significant utility.

Thus, the present invention has been described herein with reference to a particular embodiment for a particular application. Those having ordinary skill in the art and access to the present teachings will recognize additional modifications, applications and embodiments within the scope thereof.

It is therefore intended by the appended claims to cover any and all such applications, modifications and embodiments within the scope of the present invention.

What is claimed is:

1. A system for monitoring the accomplishment of an activity of a user, the system comprising:
   a network;
   an activity monitoring system for monitoring the accomplishment of physical activity of the user assigned by a supervisor supervising physical activities of the user;
   wherein the assigned physical activity is remotely accomplished away from the supervisor and the assigned physical activity specifies a specific location and time window to accomplish the physical activity;
   wherein the activity monitoring system includes data storage for storing information associated with the assigned physical activity for the user of the system;
   a server communicating with the network and the activity monitoring system; and
   an interactive communication and verification (ICV) apparatus connected to the network and includes a processor having program instructions for accumulating information related to the accomplishment of the assigned physical activity, the ICV used by the user and being located remotely away from the supervisor;
   wherein the ICV accumulates information from various sources to determine if the assigned physical activity is performed at the specific location and time window assigned by the supervisor;
   wherein the ICV apparatus utilizes a location services module for determining a location of the ICV when accomplishing the assigned task and a clock for determining a time when the assigned physical activity is accomplished;
   wherein the ICV apparatus includes programming instructions for communicating with an external monitoring device monitoring the user while performing the assigned exercise, the external monitoring device providing vital sign performance data to the ICV apparatus;
   wherein the ICV apparatus evaluates the provided vital sign or performance data received from the external monitoring device to verify the accomplishment of the assigned activity;
   wherein the processor of the ICV apparatus includes programming instructions for sending accumulated information via the network to the activity monitoring system;
   wherein the activity monitoring system receives and stores a predefined activity parameter and penalty/ accountability fee assessment for failure to complete the scheduled activity within the predefined activity parameter within the data storage;

wherein the predefined activity parameter includes information on the assigned physical activity to include the specific location and time window;

wherein the activity monitoring system includes programming instructions to determine if the assigned physical activity is performed based on the predefined activity parameter;

wherein the activity monitoring system includes programming instructions to assess the penalty/accountability fee assessment to the user for failure to complete the scheduled activity within the predefined activity parameter.

2. The system according to claim 1 further comprising a supervisor communication device, the supervisor communication device associated with a supervisor of the user related to the activity, wherein the supervisor communication device is connected to the network and configured for sending and receiving information via the network to the activity monitoring system.

3. The system according to claim 2 wherein any penalty/accountability fee collected is at least partially distributed to the supervisor.

4. The system according to claim 2 wherein the supervisor communication device includes a supervisor interface for monitoring and amending activities of a user.

5. The system according to claim 2 wherein the activity monitoring system is configured to allow communication between the user communication device and the supervisor communication device related to the activity.

6. The system according to claim 1 wherein the parameter of the activity is a location for performing the assigned physical activity and the activity monitoring system is configured for determining if a user is located within the location parameter.

7. The system according to claim 1 wherein the activity monitoring system is configured for providing information on a planned or accomplished activity to a user.

8. The system according to claim 1 wherein the activity monitoring system is configured for storing user information related to the activity for retrieval by a user or supervisor.

9. The system according to claim 1 wherein the activity monitor system is configured to determine if a user performed an activity within the predefined parameter within a predefined time and location.

10. A computer implemented method of encouraging the accomplishment of a physical activity assigned to a user, the method comprising the steps of:

assigning a physical activity of the user by a supervisor supervising physical activities of the user, wherein the assigned physical activity is remotely accomplished away from the supervisor and the assigned physical activity specifies a specific location and time window to accomplish the physical activity;

accumulating information on the accomplishment of the physical activity assigned to the user by an interactive communication and verification (ICV) apparatus, the ICV apparatus gathering information relevant for verifying the accomplishment of the assigned physical activity, the ICV being used by the user and being located remotely away from the supervisor;

wherein the ICV accumulates information from various sources to determine if the assigned physical activity is performed at the specific location and time window assigned by the supervisor;

wherein the ICV apparatus utilizes a location services module for determining a location of the ICV when accomplishing the assigned task and a clock for determining a time when the assigned physical activity is accomplished;

wherein the ICV apparatus includes programming instructions for communicating with an external monitoring device monitoring the user while performing the assigned exercise, the external monitoring device providing vital sign or performance data to the ICV apparatus:

wherein the ICV apparatus evaluates the provided vital sign or performance data received from the external monitoring device to verify the accomplishment of the assigned activity;

providing, by the ICV apparatus, the accumulated information and a predefined parameter on the assigned physical activity of the user to an activity monitoring system, the activity monitoring having a processor having program instructions for determining from the accumulated information if the assigned physical activity is accomplished; defining a penalty/accountability fee for failure to complete an activity within the predetermined activity parameter to the activity monitoring system;

determining by the activity monitoring system if the assigned physical activity is accomplished within the predefined parameter; and upon determining that the activity is not accomplished in the predefined parameter, automatically assessing the defined penalty/accountability fee to the user by the activity monitoring system.

11. The method according to claim 10 further comprising the step of providing information on the assigned physical activity of the user to a supervisor of the user.

12. The method according to claim 11 further comprising the step of distributing at least a partial portion of the penalty/accountability fee to the supervisor.

13. The method according to claim 10 wherein the step of determining by the activity monitoring system if the assigned physical activity is accomplished in the predefined parameter includes determining by the activity monitoring system if a user accomplished the assigned physical activity within a predefined time and location.

14. The system according to claim 1 wherein the external monitoring device is integrated with the ICV apparatus used by the user.

15. A system for monitoring the accomplishment of an activity of a user, the system comprising:

a network;

an activity monitoring system for monitoring the accomplishment of a physical activity of the user assigned by a supervisor supervising physical activities of the user;

wherein the assigned physical activity is remotely accomplished away from the supervisor and the assigned physical activity specifies a specific location and time window to accomplish the physical activity;

wherein the activity monitoring system includes data storage for storing information associated with the assigned physical activity for the user of the system;

a server communicating with the network and the activity monitoring system; and an interactive communication and verification (ICV) apparatus connected to the network and includes a processor having program instructions for accumulating information related to the accomplishment of the assigned physical activity, the ICV used by the user and being located remotely away from the supervisor;

wherein the ICV accumulates information from various sources to determine if the assigned physical activity is performed at the specific location and time window assigned by the supervisor;

wherein the ICV apparatus utilizes a location services module for determining a location of the ICV when accomplishing the assigned task and a clock for determining a time when the assigned physical activity is accomplished;

wherein the ICV apparatus includes programming instructions for communicating with an external monitoring device monitoring the user while performing the assigned exercise, the external monitoring device providing vital sign or performance data to the ICV apparatus;

wherein the ICV apparatus evaluates the provided vital sign or performance data received from the external monitoring device to verify the accomplishment of the assigned activity;

wherein the processor of the ICV apparatus includes programming instructions for sending accumulated information via the network to the activity monitoring system;

wherein the activity monitoring system receives and stores a predefined activity parameter and penalty/accountability fee assessment for failure to complete the scheduled activity within the predefined activity parameter within the data storage;

wherein the predefined activity parameter includes information on the assigned physical activity to include the specific location and time window;

wherein the activity monitoring system includes programming instructions to determine if the assigned physical activity is performed based on the predefined activity parameter;

wherein the activity monitoring system includes programming instructions to assess the penalty/accountability fee assessment to the user for failure to complete the scheduled activity within the predefined activity parameter.

\* \* \* \* \*